United States Patent
Zhang et al.

(10) Patent No.: US 12,240,798 B2
(45) Date of Patent: Mar. 4, 2025

(54) ELECTROLYTE, AND ELECTROCHEMICAL DEVICE AND ELECTRONIC DEVICE INCLUDING SAME

(71) Applicant: Ningde Amperex Technology Limited, Ningde (CN)

(72) Inventors: Lilan Zhang, Ningde (CN); Chao Tang, Ningde (CN); Weihua Zhu, Ningde (CN); Jianming Zheng, Ningde (CN)

(73) Assignee: Ningde Amperex Technology Limited, Ningde (CN)

( * ) Notice: Subject to any disclaimer, the term of this patent is extended or adjusted under 35 U.S.C. 154(b) by 553 days.

(21) Appl. No.: 17/573,710

(22) Filed: Jan. 12, 2022

(65) Prior Publication Data

US 2022/0153690 A1    May 19, 2022

Related U.S. Application Data

(63) Continuation of application No. PCT/CN2020/098458, filed on Jun. 28, 2020.

(30) Foreign Application Priority Data

Jul. 26, 2019  (CN) .......................... 201910683532.2

(51) Int. Cl.
| | |
|---|---|
| *C07C 255/46* | (2006.01) |
| *C07C 255/04* | (2006.01) |
| *C07C 255/05* | (2006.01) |
| *C07C 255/15* | (2006.01) |
| *C07C 255/16* | (2006.01) |
| *H01M 10/0525* | (2010.01) |
| *H01M 10/0567* | (2010.01) |
| *H01M 10/42* | (2006.01) |

(52) U.S. Cl.
CPC .......... *C07C 255/46* (2013.01); *C07C 255/04* (2013.01); *C07C 255/05* (2013.01); *C07C 255/15* (2013.01); *C07C 255/16* (2013.01); *H01M 10/0525* (2013.01); *H01M 10/0567* (2013.01); *H01M 10/4235* (2013.01); *H01M 2300/0025* (2013.01)

(58) Field of Classification Search
CPC ... C07C 255/46; C07C 255/04; C07C 255/05; C07C 255/15; C07C 255/16; H01M 10/0525; H01M 10/0567; H01M 10/4235; H01M 2300/0025
See application file for complete search history.

(56) References Cited

U.S. PATENT DOCUMENTS

| 3,110,630 A * | 11/1963 | Wolfe, Jr. ............. H01M 10/05 429/105 |
| 9,225,015 B2 * | 12/2015 | Lee ...................... H01M 12/06 |

(Continued)

FOREIGN PATENT DOCUMENTS

| CN | 101263622 A | 9/2008 |
| CN | 201210114187.9 | 4/2012 |

(Continued)

OTHER PUBLICATIONS

Jezowski (Safe and recyclable lithium-ion capacitors using sacrificial organic lithium salt, Nature Materials, vol. 17 pp. 167-173) ( Year: 2017).*

(Continued)

*Primary Examiner* — Matthew J Merkling
(74) *Attorney, Agent, or Firm* — Ladas & Parry LLP

(57) ABSTRACT

An electrolyte including one or more nitrile benzoquinone compounds, and the nitrile benzoquinone compound is selected from the group consisting of the compounds represented by formula I, formula II, and formula III:

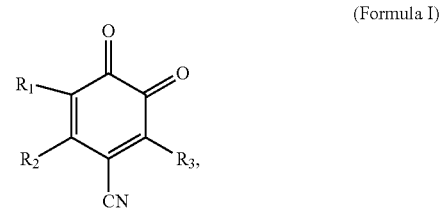

(Formula I)

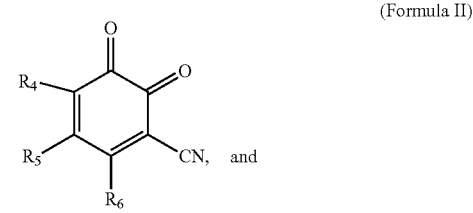

(Formula II)

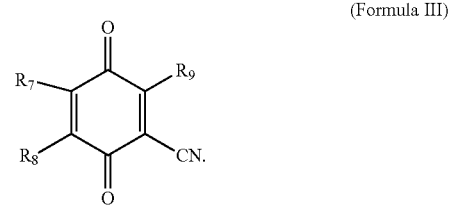

(Formula III)

The substituents $R_1$ to $R_9$ are each independently selected from the group consisting of hydrogen, a $C_2$ to $C_{12}$ ether group, a $C_1$ to $C_{12}$ alkoxy group, halogen, a $C_1$ to $C_{12}$ alkyl group, a $C_2$ to $C_{12}$ alkenyl group, a $C_2$ to $C_{12}$ alkynyl group, and a $C_6$ to $C_{26}$ aryl group. The electrolyte can form a stable protective film on a cathode, thereby increasing the cycle capacity retention rate and high temperature storage performance of an electrochemical device.

15 Claims, No Drawings

(58) Field of Classification Search
CPC ..........................................................................

(56) References Cited

U.S. PATENT DOCUMENTS

| | | | | |
|---|---|---|---|---|
| 9,825,323 | B2* | 11/2017 | Takechi | H01M 8/188 |
| 2012/0196182 | A1* | 8/2012 | Yao | H01M 4/606 |
| | | | | 568/377 |
| 2014/0335427 | A1 | 11/2014 | Khasanov et al. | |

FOREIGN PATENT DOCUMENTS

| CN | 105098235 A | 11/2015 |
|---|---|---|
| CN | 106450424 A | 2/2017 |
| CN | 107394269 A | 11/2017 |
| CN | 109244529 A | 1/2019 |
| CN | 109860703 A | 6/2019 |
| CN | 109860957 A | 6/2019 |
| CN | 110429335 A | 11/2019 |
| IN | 109411814 A | 3/2019 |
| JP | 107169505 A | 7/1995 |
| JP | H1021958 A | 1/1998 |
| JP | 2009099449 A | 5/2009 |

OTHER PUBLICATIONS

International Search Report for International Application PCT/CN2020/098458 mailed Aug. 28, 2020.

Office Action for counterpart application 201910683532.2 mailed Jul. 24, 2020.

P. Jezowski, et al.: Safe and recyclable lithium-ion capacitors using sacrificial organic lithium salt: Nature Materials | pp. 1-8 | Published Online: Dec. 11, 2017 | DOI: 10.1038/NMAT5029.

* cited by examiner

ELECTROLYTE, AND ELECTROCHEMICAL DEVICE AND ELECTRONIC DEVICE INCLUDING SAME

CROSS REFERENCE TO RELATED APPLICATIONS

The present application is a Continuation of National Stage application of PCT international application: PCT/CN2020/098458, filed on Jun. 25, 2020, which claims the benefit of priority from the China Patent Application No. 201910683532.2, filed on Jul. 26, 2019, the disclosure of which is hereby incorporated by reference in its entirety.

BACKGROUND

1. Technical Field

The present application relates to the technical field of energy storage, and more particularly to an electrolyte and an electrochemical device including the same.

2. Description of the Related Art

In order to meet the demand by people for high energy density lithium ion batteries, the voltage platform of the lithium ion batteries needs to be repeatedly improved. However, as the voltage increases, side reactions between the cathode and the electrolyte become more serious, and the particle surface layer of the cathode undergoes a phase change and is deactivated, resulting in an increase in impedance and loss of battery capacity. In addition, the electrolyte oxidizes on the surface of the cathode to form by-products and adheres to the surface of the cathode, further resulting in an increase in impedance and rapid fading of battery capacity. Therefore, it is vital to improve and optimize the composition of the electrolyte while increasing the energy density of the lithium ion batteries.

SUMMARY

The present application provides an electrolyte in an attempt to solve at least one of the problems found in the related art at least to some extent.

According to an aspect of the present application, the present application provides an electrolyte, the electrolyte includes one or more nitrile benzoquinone compounds. The nitrile benzoquinone compound is selected from the group consisting of the compounds represented by formula I, formula II, and formula III:

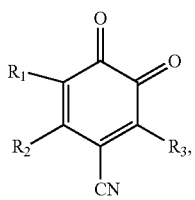

(formula I)

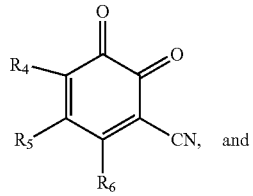

(formula II)

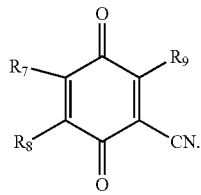

(formula III)

wherein the substituents $R_1$ to $R_9$ are each independently selected from the group consisting of hydrogen, halogen, a $C_2$ to $C_{12}$ ether group, a $C_1$ to $C_{12}$ hydrocarbyloxy group, a $C_1$ to $C_{12}$ alkyl group, a $C_2$ to $C_{12}$ alkenyl group, a $C_2$ to $C_{12}$ alkynyl group, and a $C_6$ to $C_{26}$ aryl group.

According to some embodiments of the present application, the nitrile benzoquinone compound is selected from the group consisting of the compounds represented by formula VIII-1, formula VIII-2, and formula VIII-3:

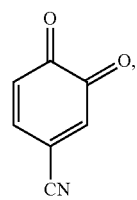

(Formula VIII-1)

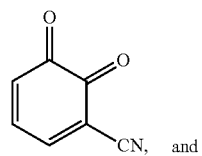

(Formula VIII-2)

and

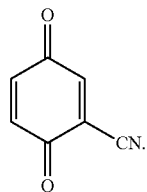

(Formula VIII-3)

According to some embodiments of the present application, a content of the nitrile benzoquinone compound is about 0.05% to about 7% based on the total weight of the electrolyte.

According to some embodiments of the present application, the electrolyte further includes at least one selected from the group consisting of: 1,3-propane sultone, fluoroethylene carbonate, and vinylene carbonate.

According to some embodiments of the present application, the electrolyte further includes one or more polynitrile compounds, and the polynitrile compound is selected from the group consisting of the compounds represented by formula IV, formula V, formula VI, and formula VII:

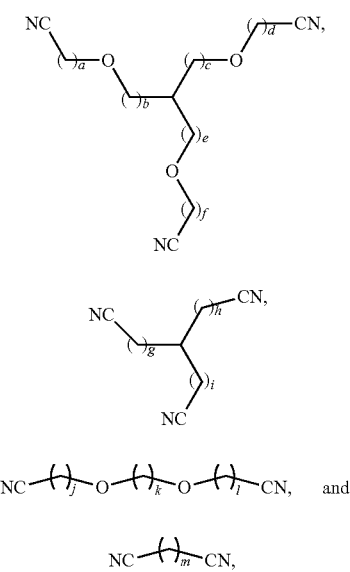

(formula IV)

(formula V)

(formula VI)

(formula VII)

wherein b, c, e, j, k and l are each independently an integer of 0 to 5, and a, d, f, g, h, i, and m are each independently an integer of 1 to 5.

According to some embodiments of the present application, the content of the polynitrile compound is about 0.1% to about 10% based on the total weight of the electrolyte.

According to some embodiments of the present application, the polynitrile compound is selected from the group consisting of the compounds represented by formula IX, formula X, formula XI, formula XII, formula XIII, and formula XIV:

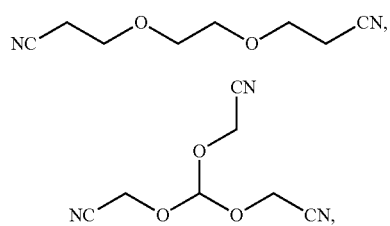

(formula IX)

(formula X)

(formula XI)

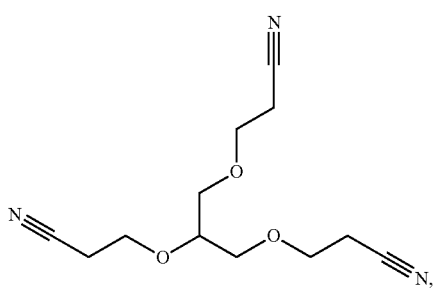

(formula XII)

(formula XIII)

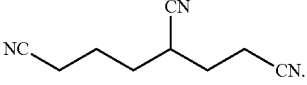

(formula XIV)

According to some embodiments of the present application, the electrolyte further includes a fluoro-ether compound, and the fluoro-ether compound includes at least one of $HCF_2CF_2CH_2OCF_2CF_2H$, $(CF_3)_2CFCF(CF_2CF_3)(OCH_3)$, $CF_3CHFCF_2CH(CH_3)OCF_2CHFCF_3$, $HCF_2CF_2CH_2OCF_2CF_2CF_2CF_2H$, $HCF_2CF_2OCH_2CF_3$, $HCF_2CF_2OCH_2CH_2OCF_2CF_2H$, $HCF_2CF_2OCH_2CH_2CH_2OCF_2CF_2H$, $HCF_2CF_2CH_2OCF_2CF_2CF_2H$, $HCF_2CF_2OCH_2CH_2OCF_2CF_2CF_2H$, $HCF_2CF_2OCH_2CH_2CH_2OCF_2CF_2CF_2H$, $CH_3OCH_2CH_2OCH_2CH_2F$, $CH_3OCH_2CH_2OCH_2CF_3$, $CH_3OCH_2CH(CH_3)OCH_2CH_2F$, $CH_3OCH_2CH(CH_3)OCH_2CF_3$, $FCH_2CH_2OCH_2CH_2OCH_2CH_2F$, $FCH_2CH_2OCH_2CH(CH_3)OCH_2CH_2F$, $CF_3CH_2O(CH_2CH_2O)_2CH_2CF_3$ or $CF_3CH_2OCH_2CH(CH_3)OCH_2CF_3$.

According to some embodiments of the present application, the electrolyte further includes a phosphate compound, and the phosphate compound includes at least one of trimethyl phosphate, triethyl phosphate, dimethyl ethyl phosphate, methyl diethyl phosphate, triphenyl phosphate, trimethyl phosphite, triethyl phosphite, triphenyl phosphite, tris(2,2,2-trifluoroethyl) phosphate or tris(2,2,3,3,3-pentafluoropropyl) phosphate.

According to some embodiments of the present application, a content of the phosphate compound is about 0.1% to about 10% based on the total weight of the electrolyte.

According to some embodiments of the present application, the electrolyte further includes sulfonate having an alkenyl group, and the alkenyl sulfonate includes at least one of 1-propene-1,3-sultone, 2-propene-1,3-sultone, 1-fluoro-1-propene-1,3-sultone, 2-fluoro-1-propene-1,3-sultone, 3-fluoro-1-propene-1,3-sultone, 1-fluoro-2-propene-1,3-sultone, 2-fluoro-2-propene-1,3-sultone, 3-fluoro-2-propene-1,3-sultone, 1-methyl-1-propene-1,3-sultone, 2-methyl-1-propene-1,3-sultone, 3-methyl-1-propene-1,3-sultone, 1-methyl-2-propene-1,3-sultone, 2-methyl-2-propene-1,3-sultone or 3-methyl-2-propene-1,3-sultone.

According to some embodiments of the present application, the sulfonate having the alkenyl group is about 0.1% to about 10% based on the total weight of the electrolyte. In some embodiments, the sulfonate having the alkenyl group is about 0.5% to about 8% based on the total weight of the electrolyte. According to another aspect of the present application, the present application provides an electrochemical device, including: a cathode, an anode, a separator, and any one of the above-mentioned electrolytes.

According to another aspect of the present application, the present application provides an electronic device, and the electronic device includes any one of the above-mentioned electrochemical devices.

According to one or more embodiments, the electrolyte of the present application is used to inhibit the oxidation reaction of the electrolyte at the cathode interface, thereby increasing the battery capacity retention rate under high temperature cycles of the electrochemical device and reducing the occurrence of gas generation under high temperature storage.

Additional aspects and advantages of the embodiments of the present application will be described or shown in the following description or interpreted by implementing the embodiments of the present application.

DETAILED DESCRIPTION

The embodiments of the present application will be described in detail below. The embodiments of the present application should not be interpreted as limitations to the present application.

As used in the present application, terms "approximately", "substantially", "essentially", and "about" are used for describing and explaining a small variation. When being used in combination with an event or circumstance, the term may refer to an example in which the event or circumstance occurs precisely, and an example in which the event or circumstance occurs approximately. For example, when being used in combination with a value, the term may refer to a variation range of less than or equal to ±10% of the value, for example, less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, if the difference between two numerical values is less than or equal to ±10% of the average of the values (e.g., less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%), the two values may be considered "substantially" the same.

In addition, sometimes, a quantity, a ratio, and another value are presented in a range format in the present application. It should be appreciated that such range formats are for convenience and conciseness, and should be flexibly understood as including not only values explicitly specified to range constraints, but also all individual values or sub-ranges within the ranges, like explicitly specifying each value and each sub-range.

In the detailed description and the claims, a list of items connected by the term "one of" or similar terms may mean any of the listed items. For example, if items A and B are listed, then the phrase "one of A and B" means only A or only B. In another example, if items A, B, and C are listed, then the phrase "one of A, B and C" means only A; only B; or only C. The item A may include a single component or multiple components. The item B may include a single component or multiple components. The item C may include a single component or multiple components.

In the detailed description and the claims, a list of items connected by the term "at least one of" or similar terms may mean any combination of the listed items. For example, if items A and B are listed, then the phrase "at least one of A and B" means only A; only B; or A and B. In another example, if items A, B and C are listed, then the phrase "at least one of A, B and C" means only A; or only B; only C; A and B (excluding C); A and C (excluding B); B and C (excluding A); or all of A, B and C. The item A may include a single component or multiple components. The item B may include a single component or multiple components. The item C may include a single component or multiple components.

Unless otherwise expressly indicated, the following terms used herein have the meanings indicated below.

The term "$C_x$" refers to containing x carbon atoms. For example, the $C_1$ to $C_{10}$ alkyl is an alkyl group having 1 to 10 carbon atoms.

The term "hydrocarbyl" encompasses alkyl, alkenyl, alkynyl, cycloalkyl, and aryl. For example, the hydrocarbyl is expected to be a linear chain hydrocarbon structure having 1 to 20 carbon atoms. The "hydrocarbyl" is also expected to be a branched chain or cyclic hydrocarbon structure having 3 to 20 carbon atoms. When the hydrocarbyl having a specific carbon number is specified, it is intended to cover all geometric isomers having such carbon number. The hydrocarbyl herein may also be a $C_1$ to $C_{15}$ hydrocarbyl group, a $C_1$ to $C_{10}$ hydrocarbyl group, a $C_1$ to $C_5$ hydrocarbyl group, a $C_5$ to $C_{20}$ hydrocarbyl group, a $C_5$ to $C_{15}$ hydrocarbyl group or a $C_5$ to $C_{10}$ hydrocarbyl group. Additionally, the hydrocarbyl can be optionally substituted. For example, the hydrocarbyl may be substituted with halogen including fluorine, chlorine, bromine and iodine, alkyl, aryl or heteroaryl.

The term "hydrocarbyloxy" refers to an L-O— group, wherein L is alkyl, alkenyl, alkynyl, cycloalkyl, and aryl. For example, when the L group is alkyl, the "hydrocarbyloxy" may be referred to as "alkoxy"; when the L group is cycloalkyl, the "hydrocarbyloxy" may be referred to as "cycloalkoxy". The hydrocarbyloxy herein may be a $C_1$ to $C_{20}$ hydrocarbyloxy group, and may also be a $C_1$ to $C_{15}$ hydrocarbyloxy group, a $C_1$ to $C_{10}$ hydrocarbyloxy group, a $C_1$ to $C_5$ hydrocarbyloxy group, a $C_5$ to $C_{20}$ hydrocarbyloxy group, a $C_5$ to $C_{15}$ hydrocarbyloxy group or a $C_5$ to $C_{10}$ hydrocarbyloxy group.

The term "alkyl" is intended to be a linear chain saturated hydrocarbon structure having 1 to 20 carbon atoms. The "alkyl" is also expected to be a branched chain or cyclic hydrocarbon structure having 3 to 20 carbon atoms. For example, the alkyl may be a $C_1$ to $C_{20}$ alkyl group, a $C_1$ to $C_{10}$ alkyl group, a $C_1$ to $C_5$ alkyl group, a $C_5$ to $C_{20}$ alkyl group, a $C_5$ to $C_{15}$ alkyl group or a $C_5$ to $C_{10}$ alkyl group. When an alkyl having a specific carbon number is specified, it may encompass all geometric isomers having that carbon number; therefore, for example, "butyl" means to include n-butyl, sec-butyl, isobutyl, tert-butyl, and cyclobutyl; and "propyl" includes n-propyl, isopropyl, and cyclopropyl. Examples of the alkyl include, but are not limited to, methyl, ethyl, n-propyl, isopropyl, cyclopropyl, n-butyl, isobutyl, sec-butyl, tert-butyl, cyclobutyl, n-pentyl, isopentyl, neopentyl, cyclopentyl, methylcyclopentyl, ethylcyclopentyl, n-hexyl, isohexyl, cyclohexyl, n-heptyl, octyl, cyclopropyl, cyclobutyl, norbornyl and the like. Additionally, the alkyl group can be optionally substituted.

The term "cycloalkyl" encompasses cyclic alkyl. The cycloalkyl may be a $C_3$ to $C_{20}$ cycloalkyl group, a $C_6$ to $C_{20}$ cycloalkyl group, a $C_3$ to $C_{10}$ cycloalkyl group, and a $C_3$ to $C_6$ cycloalkyl group. For example, the cycloalkyl may be cyclopropyl, cyclobutyl, cyclopentyl, cyclohexyl and the like. Additionally, the cycloalkyl group can be optionally substituted.

The term "alkenyl" refers to a monovalent unsaturated hydrocarbyl group which may be linear-chain or branched-chain and has at least one and usually one, two or three carbon-carbon double bonds. Unless otherwise defined, the alkenyl usually includes 2 to 20 carbon atoms, and may be, for example, a $C_2$ to $C_{20}$ alkenyl group, a $C_6$ to $C_{20}$ alkenyl group, a $C_2$ to $C_{10}$ alkenyl group or a $C_2$ to $C_6$ alkenyl group. Representative alkenyl includes (for example) ethenyl, n-propenyl, isopropenyl, n-but-2-enyl, but-3-enyl, n-hex-3-enyl and the like. Additionally, the alkenyl group can be optionally substituted.

The term "alkynyl" refers to a monovalent unsaturated hydrocarbyl group which may be linear-chain or branched-chain and has at least one and usually has 1, 2 or 3 carbon-carbon triple bonds. Unless otherwise defined, the alkynyl usually includes 2 to 20 carbon atoms, and may be, for example, a $C_2$ to $C_{20}$ alkynyl group, a $C_6$ to $C_{20}$ alkynyl group, a $C_2$ to $C_{10}$ alkynyl group or a $C_2$ to $C_6$ alkynyl group. Representative alkynyl includes (for example) ethynyl, prop-2-ynyl(n-propynyl), n-but-2-ynyl, n-hex-3-ynyl, and the like. Additionally, the alkynyl group can be optionally substituted.

The term "aryl" encompasses a monocyclic system and a polycyclic system. A polycyclic ring may have two or more rings in which two carbons are shared by two adjacent rings (where the rings are "fused"), in which at least one of the rings is aromatic and other rings may be for example, a cycloalkyl group, a cycloalkenyl group, an aryl group, a heterocyclyl group and/or a heteroaryl group. For example, the aryl group may be a $C_6$ to $C_{50}$ aryl group, a $C_6$ to $C_{40}$ aryl group, a $C_6$ to $C_{30}$ aryl group, a $C_6$ to $C_{20}$ aryl group, or a $C_6$ to $C_{10}$ aryl group. Representative aryl includes (for example) phenyl, methylphenyl, propylphenyl, isopropylphenyl, benzyl and naphthalen-1-yl, naphthalen-2-yl and the like. Additionally, the aryl group can be optionally substituted.

As used herein, the term "halogen" may be F, Cl, Br or I.

As used herein, the term "nitrile group" encompasses an organic substance containing an organic group —CN.

When the above substituents are substituted, the substituent is selected from the group consisting of halogen, an alkyl group, a cycloalkyl group, an alkenyl group, an aryl group, and a heteroaryl group.

Hereinafter, embodiments of the present application will be described in detail.

I. Electrolyte

The present application provides an electrolyte. The electrolyte can form a stable protective film on a cathode, and inhibit the oxidation reaction of the electrolyte at the cathode interface, thereby increasing the battery capacity retention rate under high temperature cycles of the electrochemical device and reducing the occurrence of gas generation under high temperature storage.

According to the present application, the electrolyte includes one or more nitrile benzoquinone compounds, and the nitrile benzoquinone compound is selected from the group consisting of the compounds represented by formula I, formula II and formula III:

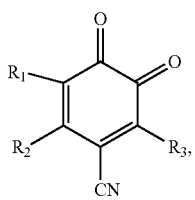
(formula I)

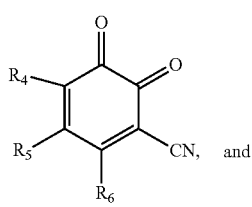
(formula II)

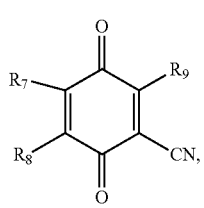
(formula III)

wherein the substituents $R_1$ to $R_9$ in the compounds represented by formula I, formula II and formula III are each independently selected from the group consisting of hydrogen, halogen, a $C_2$ to $C_{12}$ ether group, a $C_1$ to $C_{12}$ hydrocarbyloxy group, a $C_1$ to $C_{12}$ alkyl group, a $C_2$ to $C_{12}$ alkenyl group, a $C_2$ to $C_{12}$ alkynyl group, and a $C_6$ to $C_{26}$ aryl group.

In some embodiments of the present application, the nitrile benzoquinone compound is selected from the group consisting of the compounds represented by formula VIII-1, formula VIII-2, and formula VIII-3:

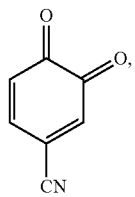
(formula VIII-1)

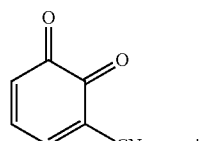
(formula VIII-2)

and

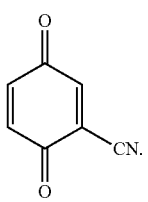
(formula VIII-3)

In some embodiments of the present application, a content of the nitrile benzoquinone compound is about 0.05% to about 7% based on the total weight of the electrolyte. In some other embodiments of the present application, the weight percentage (based on the total weight of the electrolyte) of the nitrile benzoquinone compound in the electrolyte is, for example, 0.05%, 0.1%, 0.2%, 0.5%, 1%, 2%, 3%, 4%, 5%, 6%, and 7%. The nitrile benzoquinone compound can be subjected to ring-opening polymerization to form a stable protective layer on the surface of the cathode. At the same time, due to the presence of the nitrile group, the nitrile benzoquinone compound and some active ions are subjected to a complexation reaction to further stabilize the cathode structure, and improve the stability of the cathode, ensure long cycle performance of the battery, and improve high temperature storage gas generation at the same time.

According to some embodiments of the present application, the electrolyte further includes at least one selected from the group consisting of: 1,3-propane sultone, fluoroethylene carbonate, and vinylene carbonate.

In some embodiments of the present application, a weight percentage of at least one of 1,3-propane sultone, fluoroethylene carbonate, and vinylene carbonate in the electrolyte is about 0.1% to about 15%, for example, 0.2%, 0.5%, 1%, 3%, 5%, 6%, 8%, 10%, and 12%. At least one of 1,3-propane sultone, fluoroethylene carbonate, and vinylene carbonate and the nitrile benzoquinone compound coact to form a stable protective layer on the cathode and anode surfaces to stabilize a cathode and anode interface film and improve battery cycle and storage performance.

In some embodiments of the present application, the electrolyte further includes one or more polynitrile compounds, and the polynitrile compound is selected from the group consisting of the compounds represented by formula IV, formula V, formula VI, and formula VII:

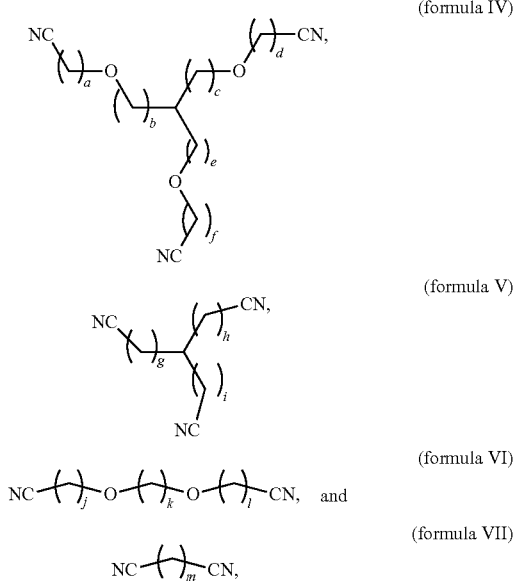

(formula IV)

(formula V)

(formula VI)

(formula VII)

wherein b, c, e, j, k and l are each independently an integer of 0 to 5, and a, d, f, g, h, i, and m are each independently an integer of 1 to 5.

In some embodiments of the present application, the polynitrile compound is selected from the group consisting of the compounds represented by formula IX, formula X, formula XI, formula XII, formula XIII, and formula XIV:

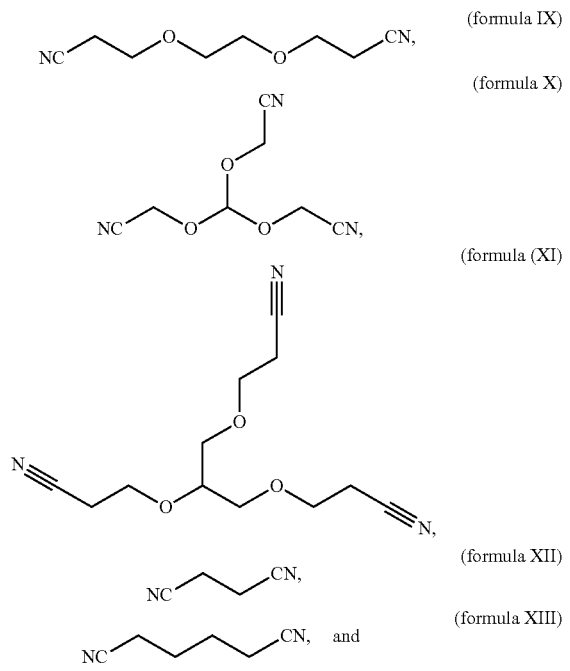

(formula IX)

(formula X)

(formula XI)

(formula XII)

(formula XIII)

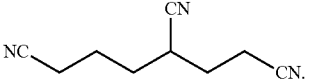

(formula XIV)

In some embodiments of the present application, a content of the polynitrile compound is about 0.1% to about 10% based on the total weight of the electrolyte. In some embodiments of the present application, the weight percentage (based on the total weight of the electrolyte) of the polynitrile compound in the electrolyte is, for example, 0.1%, 0.2%, 0.3%, 0.4%, 0.5%, 1%, 2%, 3%, 4%, 5%, 6%, 7%, 8%, 9%, and 10%.

In some embodiments of the present application, the total content of a combination of the nitrile benzoquinone compound and the polynitrile compound is about 0.3% to about 10% based on the total weight of the electrolyte. In some other embodiments of the present application, the total content of the combination of the nitrile benzoquinone compound and the polynitrile compound is about 0.5% to about 9% based on the total weight of the electrolyte. In some other embodiments of the present application, the total content of the combination of the nitrile benzoquinone compound and the polynitrile compound is about 0.7% to about 8% based on the total weight of the electrolyte. In some other embodiments of the present application, the total content of a combination of the nitrile benzoquinone compound and the polynitrile compound is about 0.9% to about 7% based on the total weight of the electrolyte. In some other embodiments of the present application, the total content of the combination of the nitrile benzoquinone compound and the polynitrile compound is about 1.5% to about 5% based on the total weight of the electrolyte.

In the present application, the nitrile benzoquinone compound and the polynitrile compound are added to a non-aqueous electrolyte to prepare the electrolyte capable of binding to active sites on the cathode and anode surfaces, for example, high-valent nickel metal ions, cobalt metal ions, manganese metal ions and the like to form a stable protective film, and the protective film can function to mask the active ions on the cathode surface, and inhibit the decomposition of other components of the electrolyte on the cathode and anode surfaces.

Therefore, in the embodiments of the present application, the addition of at least one of the nitrile benzoquinone compound and the polynitrile compound can enhance the resistance of the electrolyte containing the same to oxidation in the cathode, and form a stable protective film having lower impedance, thereby prolonging the cycle life at high voltages or high temperatures of the electrolyte and improving storage gas generation, so that the electrochemical device including the electrolyte not only exhibits good cycle performance, but also has a good storage performance in the charging and discharging processes.

In some embodiments, the electrolyte further includes a phosphate compound, and the phosphate compound includes at least one of trimethyl phosphate, triethyl phosphate, dimethyl ethyl phosphate, methyl diethyl phosphate, ethylene methyl phosphate, ethylene ethyl phosphate, triphenyl phosphate, trimethyl phosphite, triethyl phosphite, triphenyl phosphite, tris(2,2,2-trifluoroethyl) phosphate and tris(2,2,3,3,3-pentafluoropropyl) phosphate or trioctyl phosphate.

In some other embodiments of the present application, a weight percentage (based on the total weight of the electrolyte) of the phosphate compound in the electrolyte is about 0.5% to about 10%, for example, 1%, 2%, 5%, 7%, and 8%. The phosphate compound is used in combination with the nitrile benzoquinone compound to further increase the solubility of the nitrile benzoquinone compound in the electrolyte, and further improve the oxidation resistance of the electrolyte at the same time, and in the formation and recycling process, a phosphorus-nitrogen electrolyte membrane can be formed on the cathode to ensure long cycle performance of the battery.

In some embodiments, the electrolyte may include sulfonate having an alkenyl group, and the alkenyl sulfonate includes at least one of 1-propene-1,3-sultone, 2-propene-1,3-sultone, 1-fluoro-1-propene-1,3-sultone, 2-fluoro-1-propene-1,3-sultone, 3-fluoro-1-propene-1,3-sultone, 1-fluoro-2-propene-1,3-sultone, 2-fluoro-2-propene-1,3-sultone, 3-fluoro-2-propene-1,3-sultone, 1-methyl-1-propene-1,3-sultone, 2-methyl-1-propene-1,3-sultone, 3-methyl-1-prolene-1,3-sultone, 1-methyl-2-propene-1,3-sultone, 2-methyl-2-propene-1,3-sultone or 3-methyl-2-propene-1,3-sultone.

In some other embodiments of the present application, a weight percentage (based on the total weight of the electrolyte) of the sulfonate having the alkenyl group is about 0.5% to about 10%, for example, 1%, 2%, 5%, 7%, and 8%. The alkenyl sulfonate is further used in combination with the nitrile benzoquinone compound to form an SEI film having lower impedance on the surface of the electrode, thereby avoiding the high impedance problem caused by using the alkenyl sulfonate alone or the nitrile benzoquinone compound alone. At the same time, the SEI film can be repaired slowly during the destruction of a film layer in the cyclic process, thereby ensuring good cycle performance and stabilizing the growth in interface impedance.

In some embodiments of the present application, the electrolyte also includes a fluoro-ether compound, and the fluoro-ether compound includes, but is not limited to, at least one of $HCF_2CF_2CH_2OCF_2CF_2H$ (FEPE), $(CF_3)_2CFCF(CF_2CF_3)(OCH_3)$ (TMMP), $CF_3CHFCF_2CH(CH_3)OCF_2CHFCF_3$ (TPTP), $HCF_2CF_2CH_2OCF_2CF_2CF_2CF_2H$, $HCF_2CF_2OCH_2CF_3$, $HCF_2CF_2OCH_2CH_2OCF_2CF_2H$, $HCF_2CF_2OCH_2CH_2CH_2OCF_2CF_2H$, $HCF_2CF_2CH_2OCF_2CF_2CF_2H$, $HCF_2CF_2OCH_2CH_2OCF_2CF_2CF_2H$, $HCF_2CF_2OCH_2CH_2CH_2 OCF_2CF_2CF_2H$, $CH_3OCH_2CH_2OCH_2CH_2F$, $CH_3OCH_2CH_2OCH_2CF_3$, $CH_3OCH_2CH(CH_3)OCH_2CH_2F$, $CH_3OCH_2CH(CH_3)OCH_2CF_3$, $FCH_2CH_2OCH_2CH_2OCH_2 CH_2F$, $FCH_2CH_2OCH_2CH(CH_3) OCH_2CH_2F$, $CF_3CH_2O(CH_2CH_2O)_2CH_2CF_3$ or $CF_3CH_2OCH_2CH(CH_3) OCH_2CF_3$.

In some other embodiments of the present application, a weight percent (based on the total mass of the electrolyte) of the fluoro-ether compound in the electrolyte is about 0.5% to about 40%, for example, 1%, 2%, 5%, 8%, 10%, 14%, 16%, 20%, 25%, 30%, 33%, 35%, and 38%.

In some embodiments of the present application, the electrolyte also includes carboxylic anhydride, which is a compound having "—C(=O)—O—C(=O)—", and the kind thereof is not particularly limited. Examples of the carboxylic anhydride may include, but are not limited to, at least one of chain carboxylic anhydrides such as acetic anhydride and propionic anhydride, and cyclic carboxylic anhydrides such as succinic anhydride, fluorosuccinic anhydride, maleic anhydride, fluoromaleic anhydride, allyl succinic anhydride, glutaric anhydride, fluoroitaconic anhydride, or 3-sulfo-propionic anhydride.

In some other embodiments of the present application, a weight percentage of the carboxylic anhydride in the electrolyte is about 0.05% to about 10%, for example, 0.1%, 0.5%, 1%, 2%, 5%, 7%, and 8%.

In some embodiments of the present application, the electrolyte also includes a phosphazene compound, which is a compound having "—N=P—N—", and the kind thereof is not particularly limited. In some embodiments, examples of the phosphazene compound may include at least one of methoxy pentafluorocyclotriphosphazene, ethoxy pentafluorocyclotriphosphazene, phenoxy pentafluorocyclotriphosphazene or ethoxy heptafluorocyclotetraphosphazene.

In some other embodiments of the present application, a weight percentage of the phosphazene compound in the electrolyte is about 0.05% to about 10%, for example, 0.1%, 0.5%, 1%, 2%, 5%, 7%, and 8%.

In some embodiments of the present application, the electrolyte also includes a non-aqueous solvent and a lithium salt.

In some embodiments of the present application, the non-aqueous solvent includes a carbonate compound, a carboxylate compound, an ether compound, other organic solvents, or a combination thereof.

The carbonate compound can be a chain carbonate compound, a cyclic carbonate compound, a fluorocarbonate compound or a combination thereof.

The chain carbonate compound may be dimethyl carbonate (DMC), diethyl carbonate (DEC), dipropyl carbonate (DPC), methyl propyl carbonate (MPC), ethyl propyl carbonate (EPC), methyl ethyl carbonate (MEC), and a combination thereof. Examples of the cyclic carbonate compound are ethylene carbonate (EC), propylene carbonate (PC), butylene carbonate (BC), vinyl ethylene carbonate (VEC) and combinations thereof. Examples of the fluorocarbonate compound are 1,2-difluoroethylene carbonate, 1,1-difluoroethylene carbonate, 1,1,2-trifluoroethylene carbonate, 1,1,2,2-tetrafluoroethylene carbonate, 1-fluoro-2-methylethylene carbonate, 1-fluoro-1-methylethylene carbonate, 1,2-difluoro-1-methylethylene carbonate, 1,1,2-trifluoro-2-methylethylene carbonate, trifluoromethylethylene carbonate, and combinations thereof.

Examples of the carboxylate compound are methyl formate, methyl acetate, ethyl acetate, propyl propionate, n-propyl acetate, t-butyl acetate, methyl propionate, ethyl propionate, γ-butyrolactone, decalactone, valerolactone, mevalonolactone, caprolactone and a combination thereof.

Examples of the ether compound are dibutyl ether, tetraethylene glycol dimethyl ether, diethylene glycol dimetyyl ether, 1,2-dimethoxyethane, 1,2-diethoxyethane, ethoxymethoxyethane, 2-methyltetrahydrofuran, tetrahydrofuran, and a combination thereof.

Examples of other organic solvents are dimethyl sulfoxide, 1,2-dioxolane, 1,3-dioxolan, 1,4-dioxolane, sulfolane, methyl sulfolane, 1,3-dimethyl-2-imidazolidinone, N-methyl-2-pyrrolidone, formamide, dimethylformamide, acetonitrile, and a combination thereof.

In some embodiments of the present application, the lithium salt is selected from the group consisting of lithium perchlorate ($LiClO_4$), lithium hexafluorophosphate ($LiPF_6$), lithium tetrafluoroborate ($LiBF_4$), lithium tetraphenylborate ($LiB(C_6H_5)_4$), lithium methanesulfonate ($LiCH_3SO_3$), lithium trifluoromethanesulfonate ($LiCF_3SO_3$), lithium bis(trifluoromethylsulfonyl)imide ($LiN(SO_2CF_3)_2$), lithium tris(trifluoromethanesulfonate)methyl ($LiC(SO_2CF_3)_3$), lithium hexafluorosilicate ($LiSiF_6$), lithium difluorophosphate ($LiPO_2F_2$), lithium difluorooxalate borate (LiODFB), lithium dioxalate borate (LiBOB), lithium difluoroborate (LiF$_2$OB) and a combination thereof. In some embodiments of the present application, the lithium salt is selected from the group consisting of lithium hexafluorophosphate (LiPF$_6$), lithium tetrafluoroborate (LiBF$_4$), and a combination thereof.

In some embodiments of the present application, the content of the lithium salt is about 0.01 mol/L to about 3 mol/L based on the total weight of the electrolyte. In some embodiments of the present application, the content of the lithium salt is about 0.05 mol/L to about 2.2 mol/L based on the total weight of the electrolyte. In some embodiments of the present application, the content of the lithium salt is about 0.1 mol/L to about 2.2 mol/L based on the total weight of the electrolyte. In some embodiments of the present application, the content of the lithium salt is about 0.1 mol/L to about 2.0 mol/L based on the total weight of the electrolyte. It should be understood by those skilled in the art that the electrolyte of the embodiments of the present application can be manufactured by selecting any suitable known method according to actual preparation requirements, but not limited thereto.

II. Electrochemical Device

The present application also provides an electrochemical device including the electrolyte of the present application. In some embodiments of the present application, the electrochemical device is a lithium ion battery. The lithium ion battery includes a cathode, an anode, a separator, and the electrolyte of the present application.

Anode

In some embodiments of the present application, the anode used in the electrochemical device of the present application may include any of the materials, compositions, and methods for manufacturing the same disclosed in the prior art. In some embodiments, the anode is an anode disclosed in U.S. Pat. No. 9,812,739B, which is incorporated into the present application by full text reference.

In some embodiments of the present application, the anode includes an anode current collector and an anode active material layer positioned on the anode current collector. The anode active material layer includes an anode active material that absorbs and releases lithium (Li) (hereinafter, sometimes referred to as "an anode material capable of absorbing/releasing lithium Li"). In some embodiments, examples of the anode material capable of absorbing/releasing lithium (Li) may include one or more of a carbon material, a metal compound, oxide, sulfide, silicon, a silicon-carbon compound, nitride of lithium such as LiN$_3$, lithium metal, an alloy material and a polymer material.

In some embodiments, the carbon material can be any carbon-based anode active material commonly used in lithium ion batteries. In some embodiments, the carbon material includes, but is not limited to, low graphitized carbon, easily graphitized carbon, artificial graphite, natural graphite, mesocarbon microbeads, soft carbon, hard carbon, pyrolytic carbon, coke, vitreous carbon, an organic polymer compound sintered body, carbon fibers and active carbon. The coke can include pitch coke, needle coke and petroleum coke. The organic polymer compound sintered body refers to a material obtained by calcining a polymer material such as phenol plastic or furan resin at an appropriate temperature to carbonize the polymer material, and some of these materials are classified into low graphitized carbon or easily graphitized carbon. The polymer material can include polyacetylene and polypyrrole.

In some embodiments of the present application, when the anode active material includes the alloy material, the anode active material may be formed using a vapor deposition method, a sputtering method, a plating method and the like.

In some embodiments of the present application, when the anode active material includes the lithium metal or metal compound, the anode layer can include a spherical twisted conductive skeleton and metal particles dispersed in the conductive skeleton. In some embodiments of the present application, the spherical twisted conductive backbone can have a porosity of about 5% to about 85%. In some embodiments of the present application, the anode further includes a protective layer.

In some embodiments, the anode active material layer may include a binder, and optionally include a conductive agent. The binder can improve the bonding of the anode active material particles to each other and the bonding of the anode active material to the anode current collector. In some embodiments, the binder includes, but is not limited to, one or more of polyvinyl alcohol, carboxymethyl cellulose, hydroxypropyl cellulose, diacetyl cellulose, polyvinyl chloride, carboxylated polyvinyl chloride, polyvinyl fluoride, ethylene oxide containing polymers, polyvinylpyrrolidone, polyurethane, polytetrafluoroethylene, poly(1,1-difluoroethylene), polyethylene, polypropylene, styrene butadiene rubber, acrylated styrene butadiene rubber, epoxy resin, and nylon.

In some embodiments, the conductive agent includes, but is not limited to, a carbon-based material, a metal-based material, a conductive polymer and a mixture thereof. In some embodiments, the carbon-based material is selected from natural graphite, artificial graphite, carbon black, acetylene black, Ketjen black, carbon fibre or any combination thereof. In some embodiments, the metal-based material is selected from metal powder, metal fibers, copper, nickel, aluminum and silver. In some embodiments, the conductive polymer is a polyphenylene derivative.

In some embodiments, the anode current collector includes, but is not limited to, copper foil, nickel foil, stainless steel foil, titanium foil, nickel foam, copper foam, a polymer substrate coated with a conductive metal, and any combination thereof. The anode of the embodiments of the present application can be prepared by a preparation method known in the art. In some embodiments of the present application, the method for preparing the anode includes the following steps: mixing an anode active material, a conductive agent, and a binder in a solvent to prepare an anode active material composition, and coating an anode current collector with the anode active material composition. In some embodiments, the solvent may include water, but is not limited thereto.

Cathode

In some embodiments of the present application, the cathode used in the electrochemical device of the present application can be prepared using materials, structures, and manufacturing methods known in the art. In some embodiments, the cathode can be prepared using a cathode preparation technique disclosed in U.S. Pat. No. 9,812,739B, which is incorporated into the present application by full text reference.

In some embodiments, the cathode includes a cathode current collector and a cathode active material layer positioned on the cathode current collector. The cathode active material layer includes a cathode active material capable of absorbing and releasing lithium (hereinafter, sometimes referred to as "a cathode material capable of absorbing/releasing lithium"). In some embodiments, the cathode active material includes a composite oxide. In some embodiments, the cathode composite oxide may include lithium and at least one element selected from the group consisting of cobalt, manganese, and nickel.

In some embodiments of the present application, examples of the cathode material capable of absorbing/releasing lithium may include one or more of lithium cobaltate, lithium nickel cobalt manganate, lithium nickel cobalt aluminate, lithium manganate, lithium manganese iron phosphate, lithium vanadium phosphate, lithium vanadium oxide phosphate, lithium iron phosphate, lithium titanate, and a lithium-rich manganese-based material.

In some embodiments of the present application, the cathode active material layer may have a coating on its surface or may be mixed with another compound having a coating. The coating may include at least one coating element compound selected from an oxide of the coating element, a hydroxide of the coating element, an oxyhydroxide of the coating element, a bicarbonate of the coating element and a hydroxycarbonate of the coating element. The coating element compound may be amorphous or crystalline.

In some embodiments of the present application, the coating element contained in the coating may include at least one of magnesium (Mg), aluminum (Al), cobalt (Co), potassium (K), sodium (Na), calcium (Ca), silicon (Si), titanium (Ti), vanadium (V), tin (Sn), germanium (Ge), tin (Sn), boron (B), arsenic (As), gallium (Ga), zirconium (Zr), and fluorine (F). It should be understood by those skilled in the art that the coating can be applied to the cathode by any method commonly used in the art as long as the method does not adversely affect the performance of the cathode active material. In some embodiments of the present application, the method may include any coating method known in the art, such as spraying or dipping, but is not limited thereto.

In some embodiments of the present application, the cathode active material layer also includes a binder, and optionally includes a conductive agent. The binder improves the bonding of the cathode active material particles to each other, and also improves the bonding of the cathode active material to the cathode current collector.

In some embodiments of the present application, the binder includes, but is not limited to, one or more of polyvinyl alcohol, hydroxypropyl cellulose, diacetyl cellulose, polyvinyl chloride, carboxylated polyvinyl chloride, polyvinyl fluoride, ethylene oxide containing polymers, polyvinylpyrrolidone, polyurethane, polytetrafluoroethylene, poly(1,1-difluoroethylene), polyethylene, polypropylene, styrene butadiene rubber, acrylated styrene butadiene rubber, epoxy resin, and nylon.

In some embodiments of the present application, the conductive agent includes, but is not limited to, a carbon-based material, a metal-based material, a conductive polymer and a mixture thereof. In some embodiments, the carbon-based material is selected from at least one of natural graphite, artificial graphite, carbon black, acetylene black, Ketjen black, and carbon fibre. In some embodiments, the metal-based material is selected from at least one of metal powder, metal fibers, copper, nickel, aluminum and silver. In some embodiments, the conductive polymer is a polyphenylene derivative.

In some embodiments of the present application, the cathode current collector may be aluminum, but is not limited thereto.

The cathode may be prepared by a preparation method known in the art. In some embodiments of the present application, the method for preparing the cathode includes the following steps: mixing a cathode active material, a conductive agent, and a binder in a solvent to prepare a cathode active material composition, and coating a cathode current collector with the cathode active material composition. In some embodiments of the present application, the solvent may include N-methylpyrrolidone or the like, but is not limited thereto.

In some embodiments of the present application, the cathode can be produced by forming the cathode active material layer on the cathode current collector using a powder including a lithium transition metal compound and the binder.

In some embodiments, the cathode has the thickness of about 50 μm to about 200 μm. In some embodiments, the cathode has the thickness of about 60 μm to about 190 μm. In some other embodiments, the cathode has the thickness of about 60 μm to about 180 μm.

In some embodiments, the material of the cathode active material layer includes any material known in the art.

Separator

In some embodiments of the present application, the electrochemical device of the present application is provided with a separator between the cathode and the anode to prevent a short circuit. The material and shape of the separator used in the electrochemical device of the present application are not particularly limited, and may be any of the techniques disclosed in prior art. In some embodiments of the present application, the separator includes a polymer or an inorganic substance or the like formed by a material that is stable with the electrolyte of the present application.

For example, the separator may include a substrate layer and a surface treatment layer. In some embodiments of the present application, the substrate layer is nonwoven cloth, a film or a composite film having a porous structure, and the material of the substrate layer includes at least one of polyethylene, polypropylene, polyethylene terephthalate and polyimide. Specifically, a polypropylene porous film, a polyethylene porous film, polypropylene nonwoven cloth, polyethylene nonwoven cloth or a polypropylene-polyethylene-polypropylene porous composite film can be adopted.

At least one surface of the substrate layer is provided with a surface treatment layer, which may be a polymer layer or an inorganic layer, or a layer formed by mixing a polymer and an inorganic substance.

In some embodiments of the present application, the inorganic substance layer includes inorganic particles and a binder, and the inorganic particles are selected from the group consisting of alumina, silica, magnesia, titania, hafnium oxide, tin oxide, cerium oxide, nickel oxide, zinc oxide, calcium oxide, zirconium oxide, yttrium oxide, silicon carbide, boehmite, aluminum hydroxide, magnesium hydroxide, calcium hydroxide, barium sulfate, and combinations thereof. The binder is selected from the group consisting of polyvinylidene fluoride, vinylidene fluoride-hexafluoropropylene copolymer, polyamide, polyacrylonitrile, polyacrylate ester, polyacrylic acid, polyacrylate salt, polyvinylpyrrolidone, polyvinyl ether, polymethyl methacrylate, polytetrafluoroethylene, polyhexafluoropropylene and combinations thereof.

In some embodiments of the present application, the polymer layer includes a polymer, and the material of the polymer includes at least one of polyamide, polyacrylonitrile, acrylate polymer, polyacrylic acid, polyacrylate, polyvinylpyrrolidone, polyvinyl ether, polyvinylidene fluoride and poly(vinylidene fluoride-hexafluoropropylene).

It should be understood by those skilled in the art that the above described methods of preparing the lithium ion battery are merely embodiments. Other methods commonly used in the art may be employed without departing from the disclosure of the present application. Although a lithium ion battery is exemplified above, after reading this application, those skilled in the art will understand that the electrolyte of the present application can be used in other suitable electrochemical devices. Such electrochemical devices may include any device for electrochemical reaction including but not limit to all kinds of primary batteries, secondary batteries, fuel cells, solar cells or capacitors. In particular, the electrochemical device is a lithium secondary battery including a lithium metal secondary battery, a lithium ion secondary battery, a lithium polymer secondary battery or a lithium ion polymer secondary battery.

III. Electronic Device

The application further provides an electronic device, and the electronic device includes the electrochemical device of the present application.

The electronic device of the present application is not particularly limited and can be any electronic device known in the art. In some embodiments of the present application, the electronic device may include, but is not limited to, a notebook computer, a pen-input computer, a mobile computer, an e-book player, a portable phone, a portable fax machine, a portable copier, a portable printer, a head-mounted stereo headphone, a video recorder, an LCD TV, a portable cleaner, a portable CD player, a Minidisc player, a transceiver, an electronic notebook, a calculator, a memory card, a portable recorder, a radio, a backup power source, a motor, a vehicle, a motorcycle, a motorbicycle, a bicycle, a lighting apparatus, a toy, a game console, a clock, an electric tool, a flash light, a camera, a large battery for household use, or a lithium ion capacitor.

EXAMPLES

Examples and comparative examples are listed below and a high temperature cycle performance test and a high temperature storage test were respectively conducted to better illustrate the technical solutions of the present application. It will be understood by those skilled in the art that the preparation methods described in the present application are merely exemplary embodiments, and the modifications and equivalent replacements made to the technical solutions of the present application without departing from the scope of the technical solutions of the present application should fall within the scope of the protection of the present application.

(1) Preparation of Lithium-Ion Battery
Preparation of Cathode

Lithium cobaltate ($LiCoO_2$), the conductive agent Super P, and polyvinylidene fluoride were mixed according to a weight ratio of 97 to 1.4 to 1.6, added with N-methylpyrrolidone (NMP), and uniformly mixed under the action of a vacuum mixer to obtain a cathode slurry. Aluminum foil was used as the cathode current collector, the aluminum foil had the thickness of 12 μm, the surface of the cathode current collector was uniformly coated with the cathode slurry (cathode active material layer), and then the cathode current collector coated with the cathode slurry was baked at a temperature of 120° C. for 1 hour, and then subjected to cold pressing, cutting, and slitting to obtain the cathode.

Preparation of Anode

Artificial graphite, sodium carboxymethyl cellulose (CMC), and the binder styrene-butadiene rubber (SBR) were mixed according to a weight ratio of 97 to 1 to 2, and added with deionized water to obtain an anode slurry under the action of a vacuum mixer. Copper foil was used as the anode current collector, the copper foil had the thickness of 12 μm, the surface of the anode current collector was uniformly coated with the anode slurry (anode active material layer), and then the anode current collector coated with the anode slurry was baked at a temperature of 120° C. for 1 hour, and then subjected to cold pressing, cutting, and slitting to obtain the anode.

Preparation of Electrolytic Solution

In an argon atmosphere glove box with a water content of less than 10 ppm, ethylene carbonate (EC), diethyl carbonate (DEC), propylene carbonate (PC), and propyl propionate (PP) were uniformly mixed according to a weight ratio of 2 to 3 to 2 to 3, and then the sufficiently dried lithium salt $LiPF_6$ was dissolved in the above solvent to obtain a base electrolyte in which the concentration of $LiPF_6$ in the base electrolyte was about 1 mol/L. Different amounts of substances shown in the following Tables 1 to 3 were added to the base electrolyte to obtain electrolytes in different examples and comparative examples. The content of each substance in the electrolytes described below is calculated based on the total weight of the electrolyte.

Preparation of Lithium-Ion Battery

The electrolytes in the examples and comparative examples are prepared into lithium ion batteries by the following preparing method. Specifically, a polypropylene film (PP) was used as the separator, the polypropylene film had the thickness of 12 μm, and the above cathode, separator and anode were stacked in order, so that the separator was positioned between the cathode and the anode to play a separating role; then, they were wound, placed in an aluminum plastic film, and dried at a temperature of 80° C., injected with the prepared electrolyte, and subjected to vacuum encapsulation, standing, formation, shaping, and other working procedures to complete the preparation of the lithium ion battery.

After the finished lithium-ion batteries of the above examples and comparative examples were completed, the battery capacity, thickness, width and length of the finished products were recorded to determine the volumetric energy density of the lithium-ion battery. High temperature cycle performance tests and high temperature storage tests of the lithium ion batteries of the following examples and comparative examples were subsequently carried out.

(2) Testing Method
High Temperature Cycle Performance Testing

The finished lithium ion batteries of the above examples and comparative examples were placed in a 45° C. incubator, charged to 4.35 V at a constant current of 1 C, then charged to a current of 0.05 C at a constant voltage, and finally discharged to 3.0 V at a constant discharge rate of 1 C. This is a charge and discharge cycle process. After 500 charge and discharge cycles were carried out as described above, the discharge capacities at the first charge and discharge cycle and the $500^{th}$ charge and discharge cycle were recorded as the first battery capacity and the battery capacity after the charge and discharge cycle of the lithium ion battery, respectively, and the battery capacity retention rate after the $500^{th}$ charge and discharge cycle was recorded; "1 C" is the current value at which the battery capacity is completely discharged within 1 hour:

> battery capacity retention rate=battery capacity (mAh) after charge and discharge cycle/first battery capacity (mAh)×100%.

High Temperature Storage Testing

The finished lithium ion batteries of the above examples and comparative examples were placed in a 25° C. incubator, charged to 4.35 V at a constant charging rate of 1 C, and then charged to a charging rate of 0.05 C at a constant voltage, and then the lithium ion batteries were placed in a 60° C. incubator to be stored for 30 days; after being stored for 30 days, the thickness variation of the lithium ion batteries was observed and recorded:

> thickness growth rate=(thickness after high temperature storage−thickness before high temperature storage)/thickness before high temperature storage×100%.

The specific parameters of Examples 1 to 18 and Comparative Example 1 and the test results obtained by the high temperature cycle performance test and the high temperature storage test are shown in Table 1 below.

TABLE 1

| Examples/Comparative Example | Nitrile benzoquinone compounds Structural formulas | Nitrile benzoquinone compounds Content (%) | PS Content (%) | FEC Content (%) | Battery capacity retention rate | Thickness growth rate |
|---|---|---|---|---|---|---|
| Example 1 | VIII-1 | 0.1 | — | — | 81% | 13.1% |
| Example 2 | VIII-1 | 0.5 | — | — | 82% | 13.3% |
| Example 3 | VIII-1 | 1.0 | — | — | 84% | 11.2% |
| Example 4 | VIII-1 | 2 | — | — | 82% | 13.0% |
| Example 5 | VIII-1 | 3 | — | — | 81% | 12.5% |
| Example 6 | VIII-1 | 5 | — | — | 74% | 15.0% |
| Example 7 | VIII-2 | 0.5 | — | — | 76% | 13.4% |
| Example 8 | VIII-2 | 1.0 | — | — | 82% | 12.5% |
| Example 9 | VIII-3 | 0.5 | — | — | 75% | 14.3% |
| Example 10 | VIII-3 | 1.0 | — | — | 80% | 12.9% |
| Example 11 | VIII-1 | 1.0 | 1 | — | 85% | 10.9% |
| Example 12 | VIII-1 | 1.0 | — | 1 | 86% | 10.5% |
| Example 13 | VIII-1 | 1.0 | 1 | 1 | 88% | 9% |
| Example 14 | VIII-2 | 1.0 | 1 | — | 83% | 11% |
| Example 15 | VIII-2 | 1.0 | — | 1 | 84% | 11% |
| Example 16 | VIII-2 | 1.0 | 1 | 1 | 85% | 10.1% |
| Example 17 | VIII-3 | 1.0 | 1 | — | 82% | 10% |
| Example 18 | VIII-3 | 1.0 | 1 | 1 | 85% | 11% |
| Comparative Example 1 | VIII-1 | 0 | — | — | 71% | 15.1% |

It can be seen from the data in Table 1 that compared with Comparative Example 1, the nitrile benzoquinone compounds (the structural formulas thereof are formula VIII-1, formula VIII-2, and formula VIII-3 respectively) are added to Examples 1 to 10 of the present application, wherein the addition amounts of the nitrile benzoquinone compounds represented by formula VIII-1, formula VIII-2, and formula VIII-3 are between 0.1% and 5%. Compared with Comparative Example 1, the lithium ion batteries of Examples 1 to 10 of the present application have significant improvements in the test results (i.e., battery capacity retention rate and thickness growth rate) of both the high temperature cycle performance test and the high temperature storage test, wherein the battery capacity retention rates of the lithium ion batteries in Examples 1 to 10 of the present application are improved as compared with Comparative Example 1 without addition, and even when the weight percentage of the added nitrile benzoquinone compound of formula VIII-1 is 1.0%, the battery capacity retention rate can reach 84% respectively, and in addition, the thickness growth rate is significantly reduced to 11.2%.

It can be known from the above comparison that by adding the nitrile benzoquinone compound in the electrolyte, cycle efficiency of the electrochemical device of the present application is effectively enhanced and the gas generation under the duration of high temperature storage is inhibited, wherein the nitrile benzoquinone compounds represented by formula VIII-1, formula VIII-2 and formula VIII-3 can form the protective layer on the cathode during the cycle of the battery to inhibit the dissolution of cathode metal ions, and simultaneously inhibit the reaction between the electrolyte and the cathode, so that cycle and storage performance are both superior to the comparative example in which the additive is not added. Further, from the test results of Examples 12 to 19, it can be seen that when the nitrile benzoquinone compound is used together with the other additives PS and FEC to prepare the electrolyte, cycle and storage performance of the lithium ion battery can be further improved.

The specific parameters of Examples 19 to 76 and Comparative Examples 2 to 6 and the test results obtained by the high temperature cycle performance test and the high temperature storage test are shown in Table 2 below.

TABLE 2

| Examples/Comparative Examples | Nitrile benzoquinone compounds Structural formulas | Nitrile benzoquinone compounds Content (%) | Polynitrile compounds Structural formulas | Polynitrile compounds Content (%) | PS Content (%) | FEC Content (%) | Battery capacity retention rate | Thickness growth rate |
|---|---|---|---|---|---|---|---|---|
| Example 19 | VIII-1 | 1 | IX | 0.5 | — | — | 84.5% | 7.9% |
| Example 20 | VIII-1 | 1 | IX | 1 | — | — | 86% | 7.9% |
| Example 21 | VIII-1 | 1 | IX | 2 | — | — | 87% | 7.5% |
| Example 22 | VIII-1 | 1 | IX | 3 | — | — | 86% | 7.6% |
| Example 23 | VIII-1 | 5 | IX | 6 | — | — | 82.5 | 11% |
| Example 24 | VIII-1 | 1 | X | 0.5 | — | — | 85% | 8.0% |
| Example 25 | VIII-1 | 1 | X | 1 | — | — | 87% | 8.0% |
| Example 26 | VIII-1 | 1 | X | 2 | — | — | 86% | 9.1% |
| Example 27 | VIII-1 | 1 | X | 3 | — | — | 86% | 8.9% |
| Example 28 | VIII-1 | 1 | X | 1 | 1 | 1 | 88% | 7% |
| Example 29 | VIII-1 | 1 | XI | 0.5 | — | — | 87% | 8.5% |
| Example 30 | VIII-1 | 1 | XI | 1 | — | — | 87% | 8.0% |
| Example 31 | VIII-1 | 1 | XI | 2 | — | — | 86% | 9.1% |
| Example 32 | VIII-1 | 1 | XI | 3 | — | — | 86% | 8.9% |

TABLE 2-continued

| Examples/Comparative Examples | Nitrile benzoquinone compounds Structural formulas | Content (%) | Polynitrile compounds Structural formulas | Content (%) | PS Content (%) | FEC Content (%) | Battery capacity retention rate | Thickness growth rate |
|---|---|---|---|---|---|---|---|---|
| Example 33 | VIII-1 | 1 | XI | 1 | 1 | 1 | 88% | 7.6% |
| Example 34 | VIII-1 | 1 | XII | 0.5 | — | — | 85% | 8.7% |
| Example 35 | VIII-1 | 1 | XII | 1 | — | — | 88% | 8.5% |
| Example 36 | VIII-1 | 1 | XII | 2 | — | — | 87% | 9.0% |
| Example 37 | VIII-1 | 1 | XII | 3 | — | — | 85% | 8.6% |
| Example 38 | VIII-1 | 1 | XII | 1 | 1 | 1 | 88.5% | 8.2% |
| Example 39 | VIII-1 | 1 | XIV | 0.5 | — | — | 85% | 8.5% |
| Example 40 | VIII-1 | 1 | XIV | 1 | — | — | 89% | 8.1% |
| Example 41 | VIII-1 | 1 | XIV | 2 | — | — | 89% | 9.1% |
| Example 42 | VIII-1 | 1 | XIV | 3 | — | — | 87% | 8.9% |
| Example 43 | VIII-1 | 1 | XIV | 1 | 1 | 1 | 90% | 7.5% |
| Example 44 | VIII-3 | 1 | IX | 0.5 | — | — | 83.5% | 12% |
| Example 45 | VIII-3 | 1 | IX | 1 | — | — | 87% | 11% |
| Example 46 | VIII-3 | 1 | IX | 1 | 1 | | 87.5% | 9% |
| Example 47 | VIII-3 | 1 | IX | 1 | | 1 | 88% | 10% |
| Example 48 | VIII-3 | 1 | IX | 1 | 1 | 1 | 89% | 8% |
| Example 49 | VIII-3 | 1 | X | 0.5 | — | — | 85% | 10% |
| Example 50 | VIII-3 | 1 | X | 1 | — | — | 84% | 8% |
| Example 51 | VIII-3 | 1 | X | 1 | 1 | | 85% | 7% |
| Example 52 | VIII-3 | 1 | X | 1 | | 1 | 85% | 7% |
| Example 53 | VIII-3 | 1 | X | 1 | 1 | 1 | 87% | 6.8% |
| Example 54 | VIII-3 | 1 | XI | 0.5 | — | — | 85% | 13% |
| Example 55 | VIII-3 | 1 | XI | 1 | — | — | 86% | 13% |
| Example 56 | VIII-3 | 1 | XI | 1 | 1 | | 87% | 10% |
| Example 57 | VIII-3 | 1 | XI | 1 | | 1 | 86% | 11% |
| Example 58 | VIII-3 | 1 | XI | 1 | 1 | 1 | 89% | 9% |
| Example 59 | VIII-3 | 1 | XII | 0.5 | — | — | 82% | 11.6% |
| Example 60 | VIII-3 | 1 | XII | 1 | — | — | 82% | 11.5% |
| Example 61 | VIII-3 | 1 | XII | 1 | 1 | | 84% | 10.5% |
| Example 62 | VIII-3 | 1 | XII | 1 | | 1 | 86% | 10% |
| Example 63 | VIII-3 | 1 | XII | 1 | 1 | 1 | 89% | 8% |
| Example 64 | VIII-3 | 1 | XIV | 0.5 | — | — | 83% | 11% |
| Example 65 | VIII-3 | 1 | XIV | 1 | — | — | 86% | 9% |
| Example 66 | VIII-3 | 1 | XIV | 1 | 1 | | 89% | 8.6% |
| Example 67 | VIII-3 | 1 | XIV | 1 | | 1 | 88% | 9% |
| Example 68 | VIII-3 | 1 | XIV | 1 | 1 | 1 | 89% | 8% |
| Example 69 | VIII-1 | 1 | X, IX | 1 + 1 | — | — | 87.5% | 7.8% |
| Example 70 | VIII-1 | 1 | X, XII | 1 + 1 | — | — | 89% | 8.3% |
| Example 71 | VIII-1 | 1 | X, XIV | 1 + 1 | | | 90% | 8.0% |
| Example 72 | VIII-3 | / | IX | 1 | | | 81% | 13% |
| Example 73 | VIII-3 | / | X | 1 | | | 83% | 13% |
| Example 74 | VIII-3 | / | XI | 1 | | | 82% | 14% |
| Example 75 | VIII-3 | / | XII | 1 | | | 81% | 12% |
| Example 76 | VIII-3 | / | XIV | 1 | | | 81% | 12% |
| Comparative Example 2 | VIII-1 | 5 | IX | 10 | | | 75% | 15% |
| Comparative Example 3 | VIII-1 | 5 | X | 10 | | | 75% | 14% |
| Comparative Example 4 | VIII-1 | 5 | XI | 10 | | | 76% | 16% |
| Comparative Example 5 | VIII-1 | 5 | XII | 10 | | | 70% | 17% |
| Comparative Example 6 | VIII-1 | 5 | XIV | 10 | | | 73% | 14% |

It can be seen from the data in Table 2 that the nitrile benzoquinone compound of formula VIII-1 and the polynitrile compound of formula IX are added to the electrolytes of Examples 19 to 23 and Comparative Examples 2 to 6, wherein the addition amount of the nitrile benzoquinone compound of formula VIII-1 is between 0.05% and 7%, and the addition amount of the polynitrile compound of formula IX is 0.1% to 10%; compared with Comparative Example 1, the lithium ion batteries of Examples 19 to 23 are injected with the electrolyte including the nitrile benzoquinone compound and the polynitrile compound of the present application, so that high temperature cycle performance of the battery is improved.

Furthermore, the electrolytes in Examples 72 to 76 include only the polynitrile compounds (the structural formula thereof includes formula IX, formula X, formula XI, formula XII, and formula XIV, respectively); with respect to Comparative Example 1 without any addition, the battery cycle performances of the lithium ion batteries in Examples 72 to 76 are still significantly improved.

Moreover, it can be seen from Examples 19 to 71 and Comparative Examples 2 to 6 that both the nitrile benzoquinone compound and the polynitrile compound can form a protective film in the cathode, and the nitrile benzoquinone compound can be subjected to ring opening polymerization in the formation process to form a protective layer on the cathode surface. At the same time, the nitrile group can coordinate with some active ions, such as high-valent nickel ions, cobalt ions and manganese ions, to stabilize the cathode structure. At the same time, the polynitrile compound can be adsorbed on the cathode surface to insulate the electrolyte from the cathode, and the two act together to inhibit the reaction between the electrolyte and the cathode. When the total addition content of the nitrile benzoquinone compound and the polynitrile compound is 1%, the protective layer formed on the surface of the cathode material is insufficient, and the improvement effect is not obvious; when the total addition content of the nitrile benzoquinone compound and the polynitrile compound is increased to more than 11%, the protective layer is too thick, and the excessive amount of additive exacerbates side reaction of the anode surface, causing the destruction of the SEI film, which is disadvantageous for the retention of the battery capacity.

Comparing the electrolytes in Examples 19 to 71, it can be found that when the total addition amount of the nitrile benzoquinone compound (the structural formula thereof includes formula VIII-1 and formula VIII-3 respectively) and the polynitrile compound (the structural formula thereof includes formula IX, formula X, formula XI, formula XII and formula XIV respectively) is 1.5% to 4%, the battery capacity retention rate of the lithium ion battery after the cycle performance test can reach 82% to 90%, wherein the electrolyte added with 1.0% of the nitrile benzoquinone compound of formula VIII-1, 1.0% of the polynitrile compound of formula X, and 1.0% of the polynitrile compound of formula XIV in Example 71 even can allow the battery capacity retention rate of the lithium ion battery to reach 90%, and the thickness growth rate after the high temperature storage test can be as low as 8.0%.

It can be seen from the above examples that when the total addition amount of the nitrile benzoquinone compound and the polynitrile compound contained in the electrolyte is 1.5% to 4%, high temperature storage gas generation of the lithium ion battery is slowed down, indicating that it has a relatively good effect of stabilizing the interface at high temperatures, inhibits the oxidative decomposition of the electrolyte on the cathode surface, simultaneously reduces gas generation from the contact between the solvent and the anode caused by the rupture of the protective film due to the dissolution of the metal ions, and can improve the cycle performance and storage performance of the lithium-ion battery thereof most effectively. Meanwhile, as can be seen from Tables 1 and 2, the combined effect of the nitrile benzoquinone compound and the polynitrile compound is superior to the addition alone or to no addition on the improvement of the cycle performance and the energy storage performance of the electrochemical device.

In addition, the nitrile benzoquinone compound and the polynitrile compound are used together with other additives such as 1,3-propane sultone (PS) or fluoroethylene carbonate (FEC) to further improve cycle and storage performance, wherein even the thickness growth rate of the lithium ion battery in Example 53 can reach as low as 6.8%.

Furthermore, in some examples of the present application, the electrolyte of the present application can further include one or more additives selected from the group consisting of a fluoro-ether compound, a phosphate compound, and alkenyl sulfonate to further enhance cycle and storage performance of the electrochemical device including the electrolyte. In the following examples, the following exemplary compounds $(HCF_2CF_2CH_2OCF_2CF_2H$ (FEPE) (Formula XV), 1-propene-1,3-sultonee (Formula XVI) and triphenyl phosphate (Formula XVII)) will be added to the electrolyte including the nitrile benzoquinone compound and the polynitrile compound to further illustrate the beneficial effects thereof:

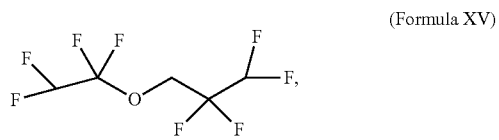

(Formula XV)

and (Formula XVI)

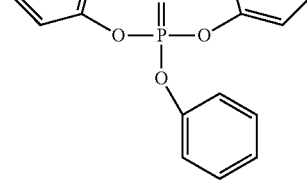

(Formula XVII)

The specific parameters of Examples 77 to 94 and the test results obtained by the high temperature cycle performance test and the high temperature storage test are shown in Table 3 below.

TABLE 3

| Examples/Comparative Examples | Nitrile benzoquinone compounds | | Polynitrile compounds | | FEC (wt %) | Additives | | Battery capacity retention rate | Thickness growth rate |
|---|---|---|---|---|---|---|---|---|---|
| | Structural formulas | Content (%) | Structural formulas | Content (%) | | Structural formulas | Content (%) | | |
| Example 77 | VIII-1 | 1 | IX | 1 | | XV | 1 | 89.50% | 7.00% |
| Example 78 | VIII-1 | 1 | IX | 1 | | XV | 2 | 88.50% | 7.10% |
| Example 79 | VIII-1 | 1 | X | 1 | | XV | 1 | 89% | 6.90% |
| Example 80 | VIII-1 | 1 | X | 1 | | XV | 2 | 89% | 7.00% |
| Example 81 | VIII-1 | 1 | XI | 1 | | XV | 1 | 90% | 7.20% |
| Example 82 | VIII-1 | 1 | XI | 1 | 2 | XV | 0.8 | 91% | 7.30% |
| Example 83 | VIII-1 | 1 | IX | 1 | | XVI | 2 | 90.50% | 7.20% |
| Example 84 | VIII-1 | 1 | IX | 1 | 1.5 | XVI | 0.5 | 90% | 7.20% |
| Example 85 | VIII-1 | 1 | X | 1 | 2 | XVI | 1 | 90% | 7.00% |
| Example 86 | VIII-1 | 1 | X | 1 | 2 | XVI | 2 | 90% | 7.20% |
| Example 87 | VIII-1 | 1 | XI | 1 | | XVI | 1 | 89.50% | 7.20% |

TABLE 3-continued

| Examples/Comparative Examples | Nitrile benzoquinone compounds | | Polynitrile compounds | | FEC (wt %) | Additives | | Battery capacity retention rate | Thickness growth rate |
|---|---|---|---|---|---|---|---|---|---|
| | Structural formulas | Content (%) | Structural formulas | Content (%) | | Structural formulas | Content (%) | | |
| Example 88 | VIII-1 | 1 | XI | 1 | | XVI | 2 | 89.50% | 7.20% |
| Example 89 | VIII-1 | 1 | IX | 1 | | XVII | 1 | 89.50% | 7.00% |
| Example 90 | VIII-1 | 1 | IX | 1 | | XVII | 2 | 89.50% | 6.90% |
| Example 91 | VIII-1 | 1 | X | 1 | | XVII | 1 | 89.50% | 7.20% |
| Example 92 | VIII-1 | 1 | X | 1 | | XVII | 2 | 89.50% | 7.40% |
| Example 93 | VIII-1 | 1 | XI | 1 | | XVII | 1 | 89.50% | 7.20% |
| Example 94 | VIII-1 | 1 | XI | 1 | | XVII | 2 | 89.50% | 7.00% |

According to the test results in Table 3, it can be seen that in Examples 77 to 94, by further adding additives (HCF$_2$CF$_2$CH$_2$OCF$_2$CF$_2$H (FEPE) (Formula XV), 1-propene-1,3-sultone (Formula XVI) and/or triphenyl phosphate (Formula XVII), high temperature cycle performance and high temperature storage performance of the lithium ion battery can be further improved, wherein the battery capacity retention rate of the lithium ion batteries in Examples 77 to 94 from the cycle performance test can reach 89.5% to 91%, and the thickness growth rate from the high temperature energy storage test can reach 6.9% to 7.3%.

According to the above examples, one of the fluoro-ether compound (formula XV) and the alkenyl sulfonate (formula XVI) used as an additive can form an SEI film on the surface of the anode, thereby reducing the reduction reaction of the metal ions on the surface of the anode to play an anode stabilizing role, and can combine the addition of the nitrile benzoquinone compound and the polynitrile compound to form an SEI film having lower impedance and higher stability on the surface of the anode; and the phosphate compound (Formula XVII) can form an SEI film on the surface of the cathode to further enhance the stability of the cathode at high voltage, and can combine the addition of the nitrile benzoquinone compound and the polynitrile compound to form an SEI film having lower impedance and higher stability on the surface of the cathode together, thereby further improving the cycle performance and storage performance at high temperatures of the electrochemical device of the present application.

It should be understood from the description of the above examples and comparative examples of the present application that the present application provides an electrolyte and an electrochemical device including the same, the electrolyte includes at least one of the nitrile benzoquinone compound and the polynitrile compound, wherein at least one of the nitrile benzoquinone compound and the polynitrile compound is not easily oxidized and can also undergo a complexation reaction with active ions, so that the electrolyte can form an SEI film having lower impedance and higher stability on the cathode and the anode, and the occurrence of side reaction on the cathode and the anode can be reduced. In the present application, cycle performance and storage performance at high voltages and high temperatures of the electrochemical device including the electrolyte can be effectively improved. Furthermore, by further including the additive such as one of a fluoro-ether compound, a phosphate compound, and alkenyl sulfonate, in the electrolyte, the cycle performance and storage performance at high voltages and high temperatures of the electrochemical device can be further improved.

Throughout the specification, references to "embodiment", "part of embodiments", "one embodiment", "another example", "example", "specific example" or "part of examples" mean that at least one embodiment or example of the present application includes specific features, structures, materials or characteristics described in the embodiment or example. Thus, the descriptions appear throughout the specification, such as "in some embodiments", "in an embodiment", "in one embodiment", "in another example", "in one example", "in a specific example" or "an example", which does not necessarily refer to the same embodiment or example in the present application. Furthermore, the specific features, structures, materials or characteristics in the descriptions can be combined in any suitable manner in one or more embodiments or examples.

Although the illustrative embodiments have been shown and described, it should be understood by those skilled in the art that the above embodiments cannot be interpreted as limitations to the present application, and the embodiments can be changed, substituted and modified without departing from the spirit, principle and scope of the present application.

What is claimed is:

1. An electrolyte, comprising: one or more nitrile benzoquinone compounds, the one or more nitrile benzoquinone compounds being selected from the group consisting of the compounds represented by formula I, formula II, and formula III:

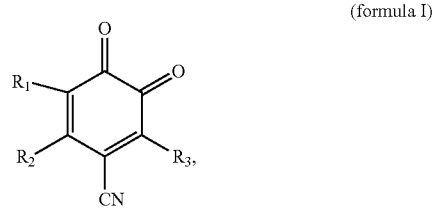

(formula I)

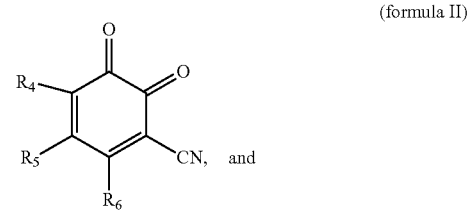

(formula II) and

-continued (formula III)

wherein the substituents $R_1$ to $R_9$ are each independently selected from the group consisting of hydrogen, halogen, a $C_2$ to $C_{12}$ ether group, a $C_1$ to $C_{12}$ hydrocarbyloxy group, a $C_1$ to $C_{12}$ alkyl group, a $C_2$ to $C_{12}$ alkenyl group, a $C_2$ to $C_{12}$ alkynyl group, and a $C_6$ to $C_{26}$ aryl group; and at least one compound selected from the group consisting of 1,3-propane sultone, fluoroethylene carbonate, and vinylene carbonate.

2. The electrolyte according to claim 1, wherein the one or more nitrile benzoquinone compounds are selected from the group consisting of the compounds represented by formula VIII-1, formula VIII-2, and formula VIII-3:

(formula VIII-1)

(formula VIII-2)

(formula VIII-3)

3. The electrolyte according to claim 1, further comprising one or more polynitrile compounds selected from the group consisting of the compounds represented by formula IV, formula V, formula VI, and formula VII:

(formula IV)

(formula V)

(formula VI)

(formula VII)

wherein b, c, e, j, k and l are each independently an integer of 0 to 5, and a, d, f, g, h, i, and m are each independently an integer of 1 to 5, wherein a content of the one or more polynitrile compounds is 0.1% to 10% based on a total weight of the electrolyte.

4. The electrolyte according to claim 3, wherein the one or more polynitrile compounds are selected from the group consisting of the compounds represented by formula IX, formula X, formula XI, formula XII, formula XIII, and formula XIV:

(formula IX)

(formula X)

(formula (XI))

(formula XII)

(formula XIII)

(formula XIV)

5. The electrolyte according to claim 1, wherein a content of the one or more nitrile benzoquinone compounds is 0.05% to 7% based on a total weight of the electrolyte.

6. The electrolyte according to claim 1, further comprising fluoro-ether compound; the fluoro-ether compound being at least one selected from $HCF_2CF_2CH_2OCF_2CF_2H$, $(CF_3)_2CFCF$ $(CF_2CF_3)(OCH_3)$, $CF_3CHFCF_2CH(CH_3)$ $OCF_2CHFCF_3$, $HCF_2CF_2CH_2OCF_2CF_2CF_2H$, $HCF_2CF_2$ $OCH_2CF_3$, $HCF_2CF_2OCH_2CH_2OCF_2CF_2H$, $HCF_2$ $CF_2OCH_2CH_2CH_2OCF_2CF_2H$, $HCF_2CF_2CH_2OCF_2$ $CF_2$ $CF_2H$, $HCF_2CF_2OCH_2CH_2OCF_2CF_2CF_2H$, HCF$_2$CF$_2$OCH$_2$CH$_2$CH$_2$OCF$_2$CF$_2$CF$_2$H, CH$_3$OCH$_2$CH$_2$OCH$_2$CH$_2$F, CH$_3$OCH$_2$CH$_2$OCH$_2$CF$_3$, CH$_3$OCH$_2$CH(CH$_3$)OCH$_2$CH$_2$F, CH$_3$OCH$_2$CH(CH$_3$)OCH$_2$CF$_3$, FCH$_2$CH$_2$OCH$_2$CH$_2$OCH$_2$CH$_2$F, FCH$_2$CH$_2$OCH$_2$CH(CH$_3$)—OCH$_2$CH$_2$F, CF$_3$CH$_2$O(CH$_2$CH$_2$O)$_2$CH$_2$CF$_3$ or CF$_3$CH$_2$OCH$_2$CH(CH$_3$)—OCH$_2$CF$_3$.

7. The electrolyte according to claim 1, further comprising a phosphate compound; the phosphate compound comprising at least one of trimethyl phosphate, triethyl phosphate, dimethyl ethyl phosphate, methyl diethyl phosphate, triphenyl phosphate, trimethyl phosphite, triethyl phosphite, triphenyl phosphite, tris(2,2,2-trifluoroethyl) phosphate or tris(2,2,3,3,3-pentafluoropropyl) phosphate.

8. An electrochemical device, comprising:

a cathode;

an anode;

a separator; and an electrolyte;

the electrolyte comprises one or more nitrile benzoquinone compounds, and at least one compound selected from the group consisting of 1,3-propane sultone fluoroethylene carbonate, and vinylene carbonate;

the one or more nitrile benzoquinone compounds being selected from the group consisting of the compounds represented by formula I, formula II, and formula III:

(Formula I)

(Formula II)

(Formula III)

wherein the substituents R$_1$ to R$_9$ are each independently selected from the group consisting of hydrogen, halogen, a C$_2$ to C$_{12}$ ether group, a C$_1$ to C$_{12}$ hydrocarbyloxy group, a C$_1$ to C$_{12}$ alkyl group, a C$_2$ to C$_{12}$ alkenyl group, a C$_2$ to C$_{12}$ alkynyl group, and a C$_6$ to C$_{26}$ aryl group.

9. The electrochemical device according to claim 8, wherein the one or more nitrile benzoquinone compounds are selected from the group consisting of the compounds represented by formula VIII-1, formula VIII-2, and formula VIII-3:

(Formula VIII-1)

(Formula VIII-2)

(Formula VIII-3)

10. The electrochemical device according to claim 8, wherein the electrolyte further comprising one or more polynitrile compounds selected from the group consisting of the compounds represented by formula IV, formula V, formula VI, and formula VII:

(formula IV)

(formula V)

(formula VI)

(formula VII)

wherein b, c, e, j, k and l are each independently an integer of 0 to 5, and a, d, f, g, h, i, and m are each independently an integer of 1 to 5, wherein a content of the one or more polynitrile compounds is 0.1% to 10% based on a total weight of the electrolyte.

11. The electrochemical device according to claim 10, wherein the one or more polynitrile compounds are selected from the group consisting of the compounds represented by formula IX, formula X, formula XI, formula XII, formula XIII, and formula XIV:

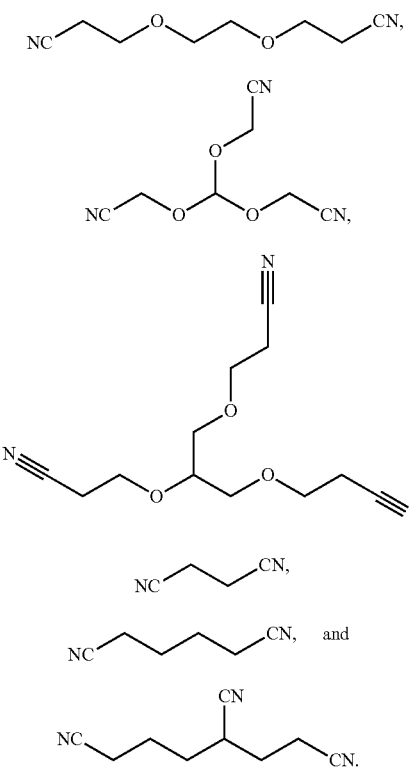

(formula IX)
(formula X)
(formula XI)
(formula XII)
(formula XIII) and
(formula XIV)

12. The electrochemical device according to claim 8, wherein a content of the one or more nitrile benzoquinone compounds is 0.05% to 7% based on a total weight of the electrolyte.

13. The electrochemical device according to claim 8, wherein the electrolyte further comprising a fluoro-ether compound; the fluoro-ether compound being at least one selected from HCF$_2$CF$_2$CH$_2$OCF$_2$CF$_2$H, (CF$_3$)$_2$CFCF(CF$_2$CF$_3$)(OCH$_3$), CF$_3$CHFCF$_2$CH(CH$_3$)OCF$_2$CHFCF$_3$, HCF$_2$CF$_2$CH$_2$OCF$_2$CF$_2$CF$_2$CF$_2$H, HCF$_2$CF$_2$OCH$_2$CF$_3$, HCF$_2$CF$_2$OCH$_2$CH$_2$OCF$_2$CF$_2$H, HCF$_2$CF$_2$OCH$_2$CH$_2$OCF$_2$CF$_2$H, HCF$_2$CF$_2$CH$_2$OCF$_2$CF$_2$CF$_2$H, HCF$_2$CF$_2$OCH$_2$CH$_2$OCF$_2$CF$_2$H, HCF$_2$CF$_2$OCH$_2$CH$_2$CH$_2$OCF$_2$CF$_2$CF$_2$H, CH$_3$OCH$_2$CH$_2$OCH$_2$CH$_2$F, CH$_3$OCH$_2$CH$_2$OCH$_2$CF$_3$, CH$_3$OCH$_2$CH(CH$_3$)OCH$_2$CH$_2$F, CH$_3$OCH$_2$CH(CH$_3$)OCH$_2$CF$_3$, FCH$_2$CH$_2$OCH$_2$CH$_2$OCH$_2$CH$_2$F, FCH$_2$CH$_2$OCH$_2$CH(CH$_3$)—OCH$_2$CH$_2$F, CF$_3$CH$_2$O(CH$_2$CH$_2$O)$_2$CH$_2$CF$_3$ or CF$_3$CH$_2$OCH$_2$CH(CH$_3$)—OCH$_2$CF$_3$.

14. The electrochemical device according to claim 8, wherein the electrolyte further comprising a phosphate compound; the phosphate compound comprising at least one of trimethyl phosphate, triethyl phosphate, dimethyl ethyl phosphate, methyl diethyl phosphate, triphenyl phosphate, trimethyl phosphite, triethyl phosphite, triphenyl phosphite, tris(2,2,2-trifluoroethyl) phosphate or tris(2,2,3,3,3-pentafluoropropyl) phosphate.

15. An electronic device, comprising an electrochemical device, wherein the electrochemical device comprises:
a cathode;
an anode;
a separator; and
an electrolyte;
the electrolyte comprises one or more nitrile benzoquinone compounds, and at least one compound selected from the group consisting of 1,3-propane sultone, fluoroethylene carbonate and vinylene carbonate;
the one or more nitrile benzoquinone compounds being selected from the group consisting of the compounds represented by formula I, formula II, and formula III:

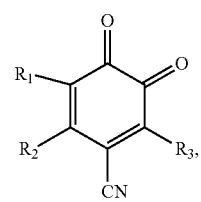

(Formula I)

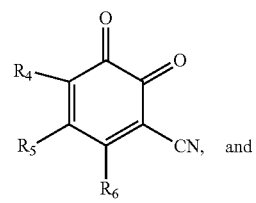

(Formula II)

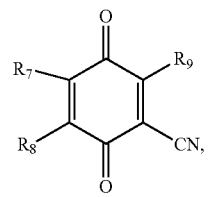

(Formula III)

wherein the substituents $R_1$ to $R_9$ are each independently selected from the group consisting of hydrogen, halogen, a $C_2$ to $C_{12}$ ether group, a $C_1$ to $C_{12}$ hydrocarbyloxy group, a $C_1$ to $C_{12}$ alkyl group, a $C_2$ to $C_{12}$ alkenyl group, a $C_2$ to $C_{12}$ alkynyl group, and a $C_6$ to $C_{26}$ aryl group.

* * * * *